US009688591B2

(12) United States Patent
Sawyer et al.

(10) Patent No.: US 9,688,591 B2
(45) Date of Patent: Jun. 27, 2017

(54) ETHYLENE SEPARATION PROCESS

(71) Applicants: Gary A. Sawyer, Media, PA (US); Robert S. Bridges, Friendswood, TX (US); Steven T. Coleman, Humble, TX (US); Allen David Hood, Jr., Houston, TX (US)

(72) Inventors: Gary A. Sawyer, Media, PA (US); Robert S. Bridges, Friendswood, TX (US); Steven T. Coleman, Humble, TX (US); Allen David Hood, Jr., Houston, TX (US)

(73) Assignees: Equistar Chemicals, LP, Houston, TX (US); Lyondell Chemical Technology, L.P., Houston, TX (US)

( * ) Notice: Subject to any disclaimer, the term of this patent is extended or adjusted under 35 U.S.C. 154(b) by 51 days.

(21) Appl. No.: 13/738,685

(22) Filed: Jan. 10, 2013

(65) Prior Publication Data

US 2014/0194664 A1    Jul. 10, 2014

(51) Int. Cl.
*C07C 4/06* (2006.01)
*C07C 7/04* (2006.01)
*C07C 6/04* (2006.01)

(52) U.S. Cl.
CPC .............. *C07C 7/04* (2013.01); *C07C 4/06* (2013.01); *C07C 6/04* (2013.01)

(58) Field of Classification Search
USPC ................. 585/643, 644; 62/620, 632, 634
See application file for complete search history.

(56) References Cited

U.S. PATENT DOCUMENTS

| 3,349,147 A * | 10/1967 | Clay et al. ............... 585/628 |
| 6,884,917 B1 * | 4/2005 | Coleman .................. 585/643 |
| 7,214,841 B2 * | 5/2007 | Gartside et al. .......... 585/324 |
| 7,525,007 B2 | 4/2009 | Sumner |
| 7,586,018 B2 * | 9/2009 | Bozzano et al. ........ 585/317 |
| 7,964,762 B2 | 6/2011 | Bouvart et al. |
| 8,586,813 B2 | 11/2013 | Ramachandran et al. |
| 2004/0254414 A1 | 12/2004 | Hildreth et al. |
| 2006/0004242 A1 * | 1/2006 | Verma et al. ............ 585/809 |
| 2006/0161033 A1 | 7/2006 | Chodorge et al. |
| 2008/0154077 A1 * | 6/2008 | Bozzano et al. ........ 585/314 |

(Continued)

FOREIGN PATENT DOCUMENTS

| EA | 014835 B1 | 2/2011 |
| RU | 2006116190 A | 12/2007 |
| WO | WO-2011113836 A1 | 9/2011 |

OTHER PUBLICATIONS

James R. Fair, "Distillation," Aug. 17, 2001, Wiley, Kirk-Othmer Encyclopedia of Chemical Technology, p. 756.*

(Continued)

*Primary Examiner* — Tam M Nguyen

(57) ABSTRACT

Ethylene separation processes are described herein. The ethylene separation processes generally include introducing a feed stream including ethylene and butene into a de-ethenizer; and separating the ethylene from the butene via fractional distillation within the de-ethenizer to form an overhead stream including separated ethylene and a bottoms stream including separated butene, wherein the de-ethenizer operates at a pressure of less than 350 psig.

6 Claims, 1 Drawing Sheet

(56) References Cited

U.S. PATENT DOCUMENTS

2010/0145120 A1* 6/2010 Bouvart .................... C07C 4/02
585/324
2012/0095275 A1 4/2012 Coleman et al.
2013/0245348 A1 9/2013 Vermeiren et al.
2014/0081061 A1* 3/2014 Stanley ................ C07C 5/2512
585/314

OTHER PUBLICATIONS

S. H. Lee et al., "Optimize design for distillation feed," Jun. 2011, Hydrocarbon Processing, p. 2.*
Singapore Search Report and Written Opinion for SG Application No. 11201504150R mailed May 3, 2016.

* cited by examiner

ETHYLENE SEPARATION PROCESS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Field of the Invention

The present invention generally relates to ethylene separation processes. More particularly, the present invention generally relates to ethylene separation within a propylene production process.

Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Ethylene separation processes within propylene production processes often exchange fresh ethylene with the feed to the ethylene separation process prior to introduction of the fresh ethylene to a metathesis reaction. However, efforts are continuously underway to improve ethylene separation processes, including reducing energy requirements and other costs in propylene production processes.

The present invention is directed to resolving, or at least reducing, one or all of the problems mentioned above.

SUMMARY

Various embodiments of the present invention include ethylene en e separation processes. The ethylene separation processes generally include introducing a feed stream including ethylene and butene into a de-ethenizer; and separating the ethylene from the butene via fractional distillation within the de-ethenizer to form an overhead stream including separated ethylene and a bottoms stream including separated butene, wherein the de-ethenizer operates at a pressure of less than 350 psig.

Various embodiments of the present invention further include processes for producing propylene. The processes generally include reacting a metathesis feed stream including butene with ethylene in the presence of a metathesis catalyst via a metathesis reaction to form a metathesis product stream including propylene, ethylene and butene; separating the ethylene from the propylene via fractional distillation within a de-ethenizer to form an overhead stream including separated ethylene and a bottoms stream including separated butene and propylene; and recycling the overhead stream from the de-ethenizer to the metathesis reaction in the form of vapor.

One or more embodiments include the process of any preceding paragraph further including compressing the overhead stream from a first pressure to a second pressure.

One or more embodiments include the process of any preceding paragraph, wherein the first pressure ranges from 250 psig to 325 psig and the second pressure ranges from 300 psig to 400 psig.

One or more embodiments include the process of any preceding paragraph, wherein a difference between the second pressure and the first pressure is from 50 psig to 100 psig.

One or more embodiments include the process of any preceding paragraph further including condensing a portion of the overhead stream to form a recycle ethylene stream and introducing the recycle ethylene stream to the de-ethenizer, wherein the overhead stream is compressed prior to condensing.

One or more embodiments include the process of any preceding paragraph, further including introducing fresh ethylene to the de-ethenizer as reflux supplement.

One or more embodiments include the process of any preceding paragraph, wherein the de-ethenizer operates at a pressure of less than 350 psig.

One or more embodiments include the process of any preceding paragraph, wherein the feed stream further including propylene.

One or more embodiments include the process of any preceding paragraph further including condensing a portion of the overhead stream to form a recycle ethylene stream and introducing the recycle ethylene stream to the de-ethenizer.

One or more embodiments include the process of any preceding paragraph, wherein the fresh ethylene is introduced to the de-ethenizer at a temperature of from −20° F. to 10° F.

One or more embodiments include the process of any preceding paragraph, wherein the metathesis product stream is introduced to the de-ethenizer at a temperature of from 50° F. to 90° F.

One or more embodiments include the process of any preceding paragraph, wherein the metathesis product stream is introduced to the de-ethenizer at a pressure of from 250 psig to 350 psig.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF DRAWINGS

The claimed subject matter may be understood by reference to the following description taken in conjunction with the accompanying drawings, in which like reference numerals identify like elements, and in which:

Figure 1:
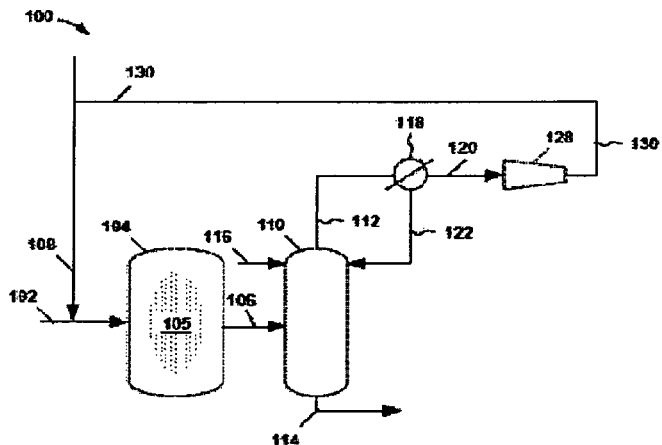
FIG. 1 illustrates an embodiment of a propylene production process.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein include ethylene separation processes. The ethylene separation processes are discussed primarily herein with reference to separating a metathesis product stream within a propylene production process. However, it is contemplated that the ethylene separation processes described herein may be utilized within any process requiring separation of ethylene from butene.

Propylene production processes generally includes reacting a metathesis feed stream including n-butene with ethylene in the presence of a metathesis catalyst to form a metathesis product stream including propylene, ethylene, butene and $C_{5+}$ olefins. As used herein, the term "metathesis" refers to an equilibrium reaction between two olefins where the double bond of each olefin is broken to form intermediate reactants. These intermediates recombine to form new olefin products. In one or more specific embodiments discussed herein, the two olefins include ethylene and butene and the new olefin product is propylene.

As discussed previously herein, n-butene is fed to the metathesis reaction via the metathesis feed stream. The ethylene may be fed to the reaction by any suitable method known to one skilled in the art. For example, the ethylene may be fed to the metathesis reaction via an inlet separate from an inlet utilized to feed the metathesis feed stream. Alternatively, the ethylene may be combined with the metathesis feed stream prior to the metathesis feed stream passing through such inlet.

Metathesis catalysts are well known in the art (see, e.g., U.S. Pat. No. 4,513,099 and U.S. Pat. No. 5,120,894). Generally, the metathesis catalyst includes a transition metal oxide, such as transition metal oxides of cobalt, molybdenum, rhenium, tungsten and combinations thereof, for example. In one or more specific embodiments, the metathesis catalyst includes tungsten oxide. The metathesis catalyst may be supported on a carrier, such as silica, alumina, titania, zirconia, zeolites, clays and mixtures thereof, for example. In one or more embodiments, the carrier is selected from silica, alumina and combinations thereof. The catalyst may be supported on a carrier by methods known in the art, such as adsorption, ion-exchange, impregnation or sublimation, for example. The metathesis catalyst may include from 1 wt. % to 30 wt. % or from 5 wt. % to 20 wt. % transition metal oxide, for example.

The metathesis reaction may further include contacting the butene with ethylene in the presence of an isomerization catalyst (either sequentially or simultaneously with the metathesis catalyst). The isomerization catalyst is generally adapted to convert 1-butene present in the metathesis feed stream to 2-butene for subsequent reaction to propylene. Isomerization catalysts may include zeolites, metal oxides (e.g., magnesium oxide, tungsten oxide, calcium oxide, barium oxide, lithium oxide and combinations thereof), mixed metal oxides (e.g., silica-alumina, zirconia-silica), acidic clays (see, e.g., U.S. Pat. No. 5,153,165; U.S. Pat. No. 4,992,613; U.S. Patent Publication 2004/0249229 and U.S. Patent Publication 2006/0084831) and combinations thereof, for example. In one or more specific embodiments, the catalyst is magnesium oxide. The magnesium oxide may have a surface area of at least 1 $m^2/g$ or at least 5 $m^2/g$, for example.

The isomerization catalyst may be supported on a support material. Suitable support materials include silica, alumina, titania, silica-alumina and combinations thereof, for example.

The metathesis reaction may occur at a pressure of from 150 psig to 600 psig, or from 200 psig to 500 psig, or from 240 psig to 450 psig, for example. The metathesis reactions may occur at a temperature of from 100° C. to 500° C., or from 200° C. to 400° C., or from 300° C. to 350° C., for example. The metathesis reaction may occur at a weight hourly space velocity (WHSV) of from 3 $hr^{-1}$ to 200 $hr^{-1}$, or from 20 $hr^{-1}$ to 40 $hr^{-1}$, for example.

The contact time needed to obtain a desirable yield of metathesis reaction products depends upon several factors, such as the activity of the catalyst, temperature and pressure, for example. However, in one or more embodiments, the length of time during which the metathesis feed stream and the ethylene are contacted with the catalyst can vary from 0.1 s to 4 hours or from 0.5 s to 0.5 hours, for example. The metathesis reaction may be conducted batch-wise or continuously with fixed catalyst beds, slurried catalyst, fluidized beds, or by using any other conventional contacting techniques, for example.

The metathesis product stream generally includes ethylene, propylene, $C_4$ olefins, and $C_{5+}$ olefins (including pentene and hexene, for example). Therefore, the propylene production process often includes separating the components of the metathesis product stream. An example of a method of separation is shown in U.S. Pat. No. 7,214,841, which is hereby incorporated by reference, and such method generally includes separation within a fractionation system. As used herein, the term "fractionation" refers to processes for the separation of components based on the relative volatility and/or boiling point of the components. The fractionation processes may include those known in the art and the term "fractionation" can be used interchangeably with the terms "distillation" and "fractional distillation" herein.

The fractionation system generally includes a de-ethenizer. The de-ethenizer receives and separates the metathesis product stream to form an overhead stream and a bottoms stream. The overhead stream is composed primarily of the recovered ethylene and at least a portion of the overhead stream may be recycled back to the metathesis reaction (discussed in further detail below). The bottoms stream generally includes the propylene, butene and $C_{5+}$ olefins.

Reflux is a distillation technique involving the condensation of vapors and the return of this condensate to the system from which it originated. Inside the distillation column, the downflowing reflux liquid provides cooling and condensation of the upflowing vapors, thereby increasing the efficiency of the distillation column. Typically, the reflux liquid is the portion of the overhead stream from a distillation column that is returned to the upper part of the column. Often, the entire de-ethenizer overhead stream is condensed to form a condensed stream, which may then be split into a reflux liquid stream and a recycle ethylene stream. In such processes, the recycle ethylene stream is returned to the metathesis reaction in liquid form.

One or more embodiments include partially condensing the overhead stream to form a reflux liquid stream and a recycle ethylene stream, which may then be returned to the metathesis reaction in vapor form. Alternatively, when no portion of the overhead product will be utilized as reflux liquid, it is contemplated that the overhead stream may be recycled (i.e., returned to the metathesis reaction) without passing through a condenser.

When recycling ethylene as vapor to the metathesis reaction, the ethylene vapor may be compressed via a compressor from a first pressure to a second pressure sufficient to provide flow of the ethylene vapor to the metathesis reaction. In one or more embodiments, the first pressure may range from 250 psig to 325 psig and the second pressure may range from 300 psig to 400 psig, for example. Alternatively, the difference in the first pressure and the second pressure may be from 50 psig to 100 psig, for example. One specific embodiment includes compressing the overhead product to raise the condensing temperature utilized in a subsequent partial condenser.

One or more embodiments include introducing fresh ethylene to the upper portion of the de-ethenizer, either in addition to, or as a replacement for the reflux liquid stream. Accordingly, the fresh ethylene introduced to the de-ethenizer is referred to as reflux supplement herein. As known in the art, "fresh" ethylene refers to ethylene that has not been processed in the system being referred to, herein the propylene production process. In one or more embodiments, the fresh ethylene is introduced to the de-ethenizer as reflux supplement at a rate that is less than that of the reflux liquid stream.

In one or more embodiments, the fresh ethylene/reflux supplement is introduced to the de-ethenizer at a temperature of from −20° F. to 100° F., or from −10° F. to 50° F., or from −10° F. to 10° F. and a pressure of from 300 psig to 1000 psig, or from 400 psig to 900 psig, or from 600 psig to 800 psig, for example.

Generally, a de-ethenizer within a propylene production process operates at a pressure of from 350 psig to 650 psig However, one or more embodiments of the present invention include operating the de-ethenizer at a pressure lower than that referenced. For example, one or more embodiments include operating the de-ethenizer at a pressure of less than 350 psig, or a pressure of less than 300 psig, or a pressure of less than 250 psig.

The fractionation system, in one or more embodiments, may further include a de-propenizer and a de-butenizer as known in the art. The de-propenizer may receive and separate the bottoms stream (from the de-ethenizer) to form a de-propenizer overhead stream and a de-propenizer bottoms stream. The de-propenizer overhead stream is composed primarily of the propylene product. The de-propenizer bottoms stream generally includes the butene and $C_{5+}$ olefins.

The de-butenizer may receive and separate at least a portion of the de-propenizer bottoms stream to form a de-butenizer overhead stream and a de-butenizer bottoms stream. The de-butenizer overhead stream is composed primarily of the recovered butene and the de-butenizer bottoms stream generally includes the $C_{5+}$ olefins. Optionally, at least a portion of the de-butenizer overhead stream may be recycled back to the metathesis reaction.

The processes described herein advantageously can reduce heating requirements in the metathesis reactor and/or the de-ethenizer, possibly by half of heating requirements for similar systems absent the embodiments of the invention. For example, embodiments described herein provide for a metathesis product stream entering the de-ethenizer having a temperature of from 50° F. to 90° F. and a pressure of from 250 psig to 350 psig, which may eliminate the need for heat exchange of the metathesis product stream.

It is noted, however, that while the addition of a compressor for the ethylene recycle stream may add capital cost to the process, lower system pressures in the metathesis reaction and the de-ethenizer can offset the compressor capital cost.

Referring now to FIG. 1, a simplified process flow diagram of a process 100 for producing propylene according to embodiments disclosed herein is illustrated. FIG. 1 illustrates a process 100 including introducing a metathesis feed stream 102 to a metathesis reactor 104 having metathesis catalyst 105 (and optional isomerization catalyst—not shown) disposed therein to form metathesis product stream 106 including propylene, ethylene, butene and $C_{5+}$ olefins. FIG. 1 illustrates a specific embodiment wherein ethylene is mixed with the metathesis feed stream 102 via line 108; however, it is contemplated that the ethylene may contact the metathesis feed stream via processes known in the art.

The metathesis product stream 106 is passed to a de-ethenizer 110 to separate at least a portion of the ethylene from the metathesis product stream 106 to form an overhead stream 112 and a bottoms stream 114 including propylene and $C_{4+}$ olefins.

Fresh ethylene is introduced to the de-ethenizer 110 as reflux supplement (in the same manner as the reflux liquid ethylene is introduced to the de-ethenizer 110) via line 116. In the specific embodiment illustrated in FIG. 1, the overhead stream 112 is passed through a partial condenser 118 to form a recycle ethylene stream 120 and a reflux liquid stream 122. The recycle ethylene stream 120 is withdrawn from the partial condenser 118 as a vapor and is compressed in compressor 128 and then recycled to the metathesis reactor 104 via line 130. The reflux liquid stream 122 is returned to the de-ethenizer 110.

Figure 2:
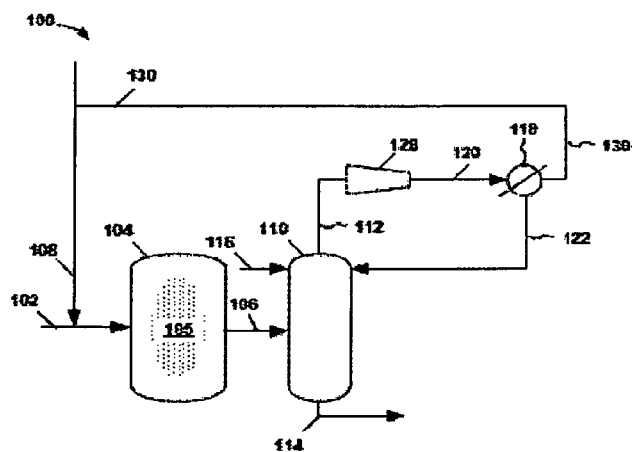
FIG. 2 illustrates an alternate embodiment of a propylene production process.

Conversely, as shown in FIG. 2, the overhead stream 112 may be compressed within the compressor 128 prior to passing through the partial condenser 118, resulting in a higher condensing temperature than that shown in FIG. 1.

As known in the art, the de-ethenizer bottoms stream 114 may be passed through a re-boiler (not shown) and returned to the de-ethenizer 110 or further separated in additional separation columns (not shown).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A process for producing ethylene comprising:
   introducing a feed stream comprising ethylene, propylene and butene into a de-ethenizer at a temperature of from 50-90° F. and a fresh ethylene stream is introduced to the de-ethenizer at a temperature of −20 to 10° F. and a pressure of 400-900 psig;
   separating the ethylene from the butene via fractional distillation within the de-ethenizer to form an overhead stream comprising separated ethylene and a bottoms stream comprising separated butene;
   wherein the de-ethenizer operates at a pressure of less than 350 psig.

2. The process of claim 1, further comprising condensing a portion of the overhead stream to form a recycle ethylene stream and introducing the recycle ethylene stream to the de-ethenizer.

3. A process for producing propylene comprising:
   reacting a metathesis feed stream comprising butene with ethylene in the presence of a metathesis catalyst via a metathesis reaction to form a metathesis product stream comprising propylene, ethylene and butene;
   introducing the metathesis product stream at a temperature of 50-90° F. and a pressure of 250-350 psig and a fresh ethylene stream at a temperature of −20 to 10° F. into a de-ethenizer;
   separating the ethylene from the propylene and butene via fractional distillation within a de-ethenizer using the ethylene separation process of claim 1 to form an overhead stream composed primarily of separated ethylene and a bottoms stream comprising separated butene and propylene; and
   recycling the overhead stream from the de-ethenizer to the metathesis reaction in the form of vapor.

4. The ethylene separation process of claim 1, wherein fresh ethylene is introduced to the de-ethenizer at a pressure of from 400-900 psig.

5. The process of claim 3, wherein the de-ethenizer operates at a pressure of less than 300 psig.

6. A process for producing propylene comprising:
   reacting a metathesis feed stream comprising butene with ethylene in the presence of a metathesis catalyst via a metathesis reaction to form a metathesis product stream comprising propylene, ethylene and butene;
   separating the ethylene from the propylene and butene via fractional distillation within a de-ethenizer using the ethylene separation process of claim 1 to form an overhead stream composed primarily of separated ethylene and a bottoms stream comprising separated butene and propylene;
   recycling the overhead stream from the de-ethenizer to the metathesis reaction in the form of vapor;
   introducing fresh ethylene at a temperature of −20 to 10° F. into the de-ethenizer at a pressure of from 400-900 psig.

* * * * *

UNITED STATES PATENT AND TRADEMARK OFFICE
CERTIFICATE OF CORRECTION

PATENT NO.         : 9,688,591 B2                                    Page 1 of 1
APPLICATION NO.    : 13/738685
DATED              : June 27, 2017
INVENTOR(S)        : Gary A. Sawyer et al.

It is certified that error appears in the above-identified patent and that said Letters Patent is hereby corrected as shown below:

In the Specification

Column 1    Line 45    After "ethylene", delete "en e"

Signed and Sealed this
Twenty-eighth Day of January, 2020

Andrei Iancu
*Director of the United States Patent and Trademark Office*